United States Patent
Manley et al.

(10) Patent No.: US 11,553,929 B2
(45) Date of Patent: *Jan. 17, 2023

(54) ATTACHMENT FOR A POWERED SURGICAL TOOL

(71) Applicant: Stryker European Operations Holdings LLC, Kalamazoo, MI (US)

(72) Inventors: Kevin Manley, Cobh (IE); Richard F. Huyser, Kalamazoo, MI (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 451 days.

This patent is subject to a terminal disclaimer.

(21) Appl. No.: 16/736,906

(22) Filed: Jan. 8, 2020

(65) Prior Publication Data

US 2020/0138453 A1 May 7, 2020

Related U.S. Application Data

(63) Continuation of application No. 15/471,004, filed on Mar. 28, 2017, now Pat. No. 10,537,339, which is a continuation of application No. PCT/US2015/053096, filed on Sep. 30, 2015.

(60) Provisional application No. 62/058,169, filed on Oct. 1, 2014.

(51) Int. Cl.
*A61B 17/16* (2006.01)
*A61B 17/00* (2006.01)

(52) U.S. Cl.
CPC ...... *A61B 17/1615* (2013.01); *A61B 17/1628* (2013.01); *A61B 17/1633* (2013.01); *A61B 17/1644* (2013.01); *A61B 17/1622* (2013.01); *A61B 17/1631* (2013.01); *A61B 2017/00473* (2013.01); *A61B 2017/1651* (2013.01); *A61B 2217/007* (2013.01)

(58) Field of Classification Search
CPC ........ A61B 17/1615; A61B 2017/1651; A61B 2017/1653; A61B 17/162
See application file for complete search history.

(56) References Cited

U.S. PATENT DOCUMENTS

| | | |
|---|---|---|
| 3,791,660 A | 2/1974 | Bostley |
| 5,405,348 A | 4/1995 | Anspach et al. |
| 5,888,200 A | 3/1999 | Walen |
| 6,132,448 A | 10/2000 | Perez et al. |
| 6,312,438 B1 | 11/2001 | Adams |
| 6,533,749 B1 | 3/2003 | Mitusina et al. |
| 6,562,055 B2 | 5/2003 | Walen |
| 6,638,289 B1 | 10/2003 | Johnson et al. |
| 7,066,940 B2 | 6/2006 | Riedel |

(Continued)

OTHER PUBLICATIONS

EPO, "ISA Search Report and Written Opinion for PCT/US2015/053096", dated Dec. 23, 2015.

*Primary Examiner* — Andrew Yang
(74) *Attorney, Agent, or Firm* — Howard & Howard Attorneys PLLC

(57) ABSTRACT

A front end attachment for a powered surgical tool comprises a nose and an irrigation fitting. The nose extends forward from a proximal end of the nose. The nose defines a bore and an enclosed channel. The bore is for receiving a cutting accessory for movement therein. The enclosed channel extends longitudinally and helically along the nose such that, as the channel extends longitudinally, the channel curves around the nose so as to curve around the bore. The irrigation fitting is received by the enclosed channel in the nose.

20 Claims, 8 Drawing Sheets

(56) References Cited

U.S. PATENT DOCUMENTS

| | | |
|---|---|---|
| 8,273,097 B2 | 9/2012 | Malla et al. |
| 8,597,316 B2 | 12/2013 | McCombs |
| 10,537,339 B2 | 1/2020 | Manley et al. |
| 2005/0177168 A1 | 8/2005 | Brunnett et al. |
| 2010/0286698 A1 | 11/2010 | Del Rio et al. |
| 2011/0270293 A1 | 11/2011 | Malla et al. |
| 2014/0107688 A1 | 4/2014 | Malla et al. |

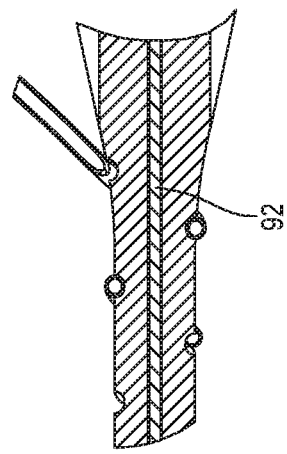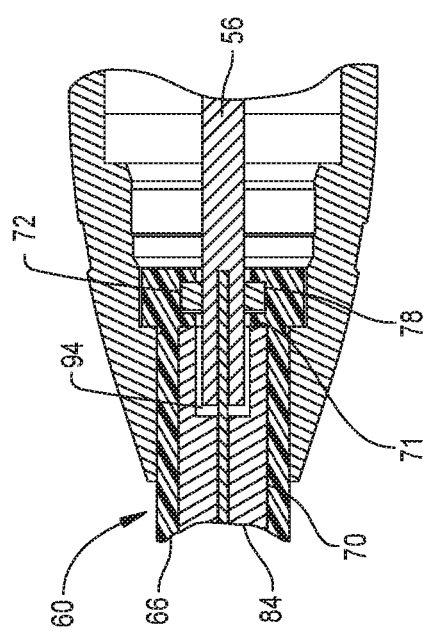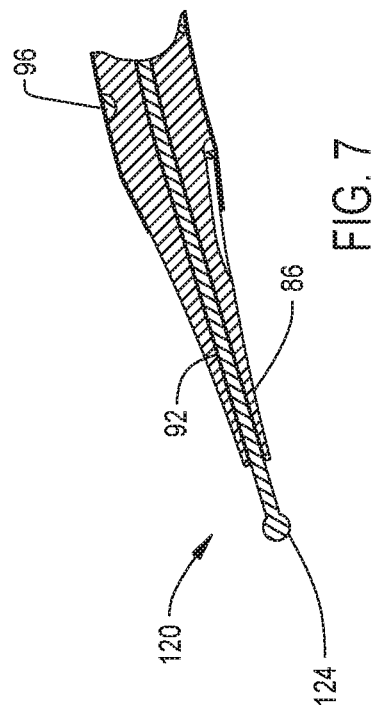

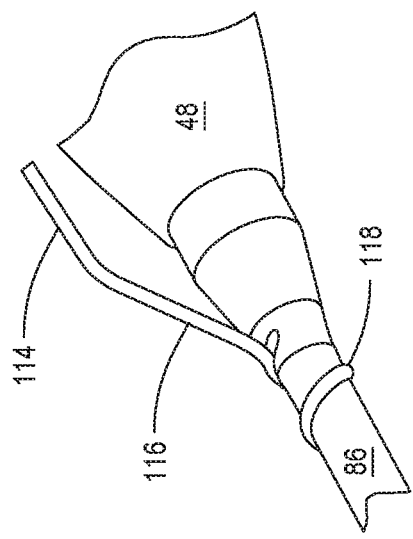
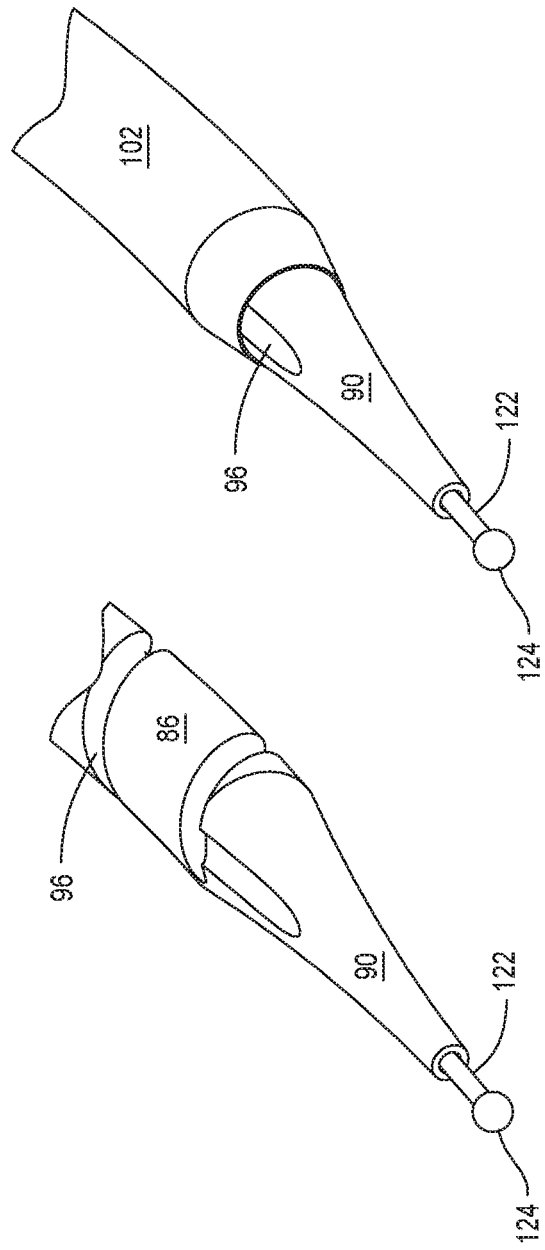

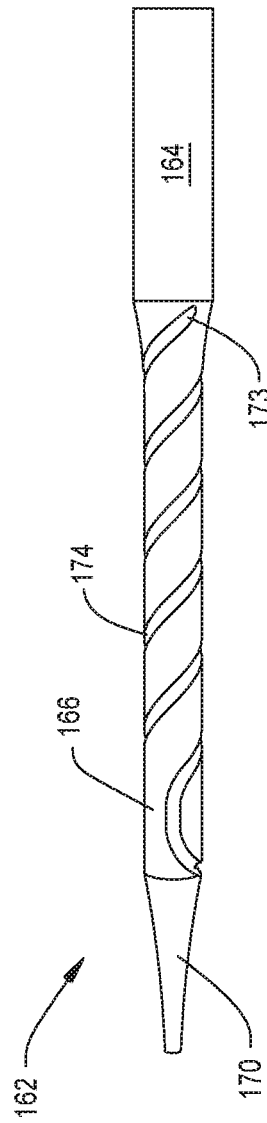
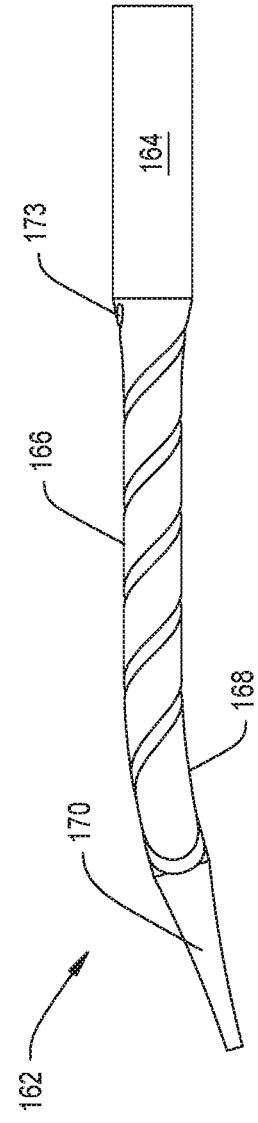
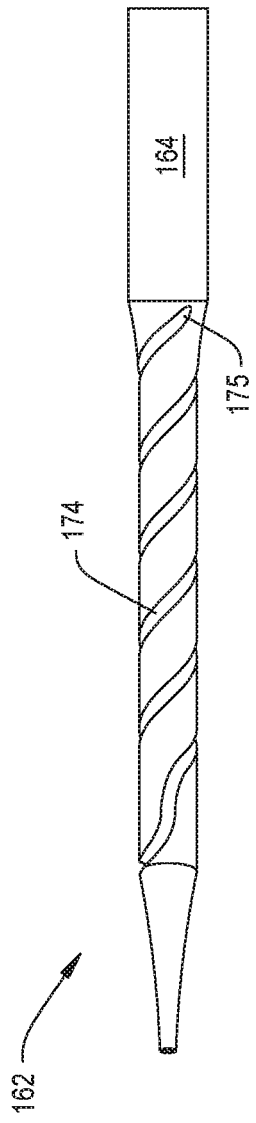
FIG. 15A
FIG. 15B
FIG. 15C

ATTACHMENT FOR A POWERED SURGICAL TOOL

RELATED APPLICATIONS

This application is a continuation of U.S. patent application Ser. No. 15/471,004, with a filing date of Mar. 28, 2017, which is a continuation of International Application No. PCT/US2015/053096, filed Sep. 30, 2015, which claims priority to U.S. Provisional patent application No. 62/058,169 filed on Oct. 1, 2014, the contents of each of which are hereby incorporated by reference as if set forth in their entireties.

FIELD OF THE INVENTION

The present invention relates generally to a powered surgical tool that includes a cutting accessory with an elongated shaft that is either rotated or reciprocated. More particularly, this invention relates to a powered surgical tool with a means to cool the accessory shaft.

BACKGROUND OF THE INVENTION

In modern surgery, one of the most important instruments available to medical personnel is the powered surgical tool. Typically, this tool comprises a handpiece in which a motor is housed. Secured to the handpiece is an accessory. The accessory is designed for application to a surgical site on a patient to accomplish a specific medical task. Some powered surgical tools are provided with drills or burs for cutting bores into hard tissue or for selectively removing the hard tissue. Still other powered surgical tools are provided with saw blades as cutting accessories. These tools are used for separating large sections of hard and/or soft tissue. The ability to use powered surgical tools on a patient has lessened the physical strain of physicians and other medical personnel when performing procedures on a patient. Moreover, most surgical procedures can be performed more quickly, and more accurately, with powered surgical tools than with the manual equivalents that preceded them.

The Applicant's Assignee's U.S. Pat. No. 5,888,200, (PCT Pub. No. WO 98/005261) entitled, MULTI-PURPOSE SURGICAL TOOL SYSTEM, incorporated herein by reference, discloses a surgical tool system designed for a number of different applications. This tool system includes a handpiece in which a motor is housed. A first coupling assembly, also part of the handpiece, for selectively couples the shaft of an accessory to the motor shaft. This handpiece also includes a second coupling assembly. The second coupling assembly selectively secures an attachment to the front end of the handpiece. The second attachment includes an elongated nose as the distalmost portion of the attachment. Often internal to the attachment are bearings. The bearings provide a low friction interface between the moving shaft of the cutting accessory and the attachment nose which is static.

The nose of this type of surgical tool system thus performs two functions. First, some of these shafts tend to be small in size, 5 mm or less in diameter. Owing to the material from which these shafts are made and their size, the shafts are, when exposed to side loading, prone to undesirable bending. This bending occurs as a result of the distal end of the shaft, when pressed against tissue to perform a procedure, is subjected to appreciable side loading. Encapsulating an accessory shaft in a nose prevents this bending.

Secondly, the nose encapsulates the moving shaft. This prevents the shaft from contacting and entraining tissue that is not to be subject to which the cutting accessory is applied. This is especially important when the system is applied to tissue located more than a centimeter from the outer skin of the patient. If the location to which the cutting accessory applied is further below skin level and the rotating shaft is unexposed a practitioner might have to form an incision in the patient that is wider than the diameter of the shaft. This wide incision would be necessary to reduce the likelihood that the moving shaft could inadvertently contact tissue that should not be exposed to the moving shaft.

Present nose assemblies prevent undesirable side bending of accessory shafts and prevent the undesirable exposure of these shafts. However, a disadvantage of some nose assemblies is that, when the accessory is actuated a significant amount of friction induced heat is developed at the locations where the moving shaft abuts the components of the nose. This heat is conducted to exposed surfaces of the nose and to other portions of the accessory, including the exposed tip. When these surfaces of the tool system contact the tissue, the heat is transferred to the tissue. This heat has the potential of damaging healthy tissue that should otherwise not be affected by the procedure. This is especially true with nose assemblies that are relatively small in diameter, less than 1 cm. Owing to the size of these noses, it has proven difficult to fit a bearing assembly able to reduce the quantity of friction induced heat that is generated. Instead, inside this type of nose, the rotating shaft often abuts the inner wall of the nose that defined the bore in which the shaft is disposed.

This undesirable heating is especially prone to occur if the nose is what is referred to as a bent nose. As implied by its name a bent nose is a nose that is formed with a bend. Often this bend is within 3 cm of the distal end of the shaft. A surgeon may want to use a surgical tool with a bent nose for a number of reasons. These reasons all root from the fact that, since the nose is bent, the exposed end of the cutting accessory, the end applied to the tissue, is spaced away from the main body nose. One advantage of the cutting accessory being so spaced from the many body of the nose is that when looking down the nose, it is easier to view this end of the accessory as well as the tissue against which the cutting accessory is applied. Further, there are times when owing to the nature of the procedure being performed the surgeon would rather position the cutting accessory laterally against the tissue than longitudinally. Having the cutting accessory extend sidewise away from the main body of the nose facilitates this type of positioning of the cutting accessory.

A tool system with bent nose, by its very nature is formed with a bore that has a bend in the vicinity of the bend in the nose. The cutting accessory used with this type of tool system has a shaft that must be flexible enough to bend in the bent section of the nose bore. Thus, as a consequence of the nature of the components forming this type of system is that as the shaft rotates in the nose, the section of the shaft in the bent section of the nose would have a tendency to rub against the inner wall of the nose that defines the nose. This movement of the shaft against the static surface can be a significant source of friction induced heating of the nose.

A number of solutions have been proposed to either eliminate or reduce this undesirable heating. As mentioned above, one solution is to fit low friction bearings in the nose to eliminate the friction induced heating. Again, when the nose itself is relatively small in diameter this solution is often commercially impracticable. Another solution is to provide a cutting accessory used with this type of nose with a shaft that is of varying diameter. Specifically, the shaft is designed so the section of the shaft that is seated in the bent section of the bore has a diameter less than the diameters of the sections of the shaft that are seated in the straight section of the bore. When this type of shaft rotates, the narrow diameter section of the shaft has minimal if any contact with the surrounding bore-defining inner wall of the nose. This reduces the frictional heating of the nose in the vicinity of the bend. However, a disadvantage of this design is that the narrow diameter section of the shaft is structurally weaker than the rest of the shaft. When the tool is actuated, owing to this section of the shaft be repeatedly bent, this section of the shaft is subjected to appreciable mechanical stress. The combination of this section of the shaft being structurally weak and being subjected to appreciable bending increases the likelihood that, in the course of a procedure, this section of the shaft will be stressed to the point where the section breaks. Should this event occur, the procedure must be interrupted to both collect the separated parts of the cutting accessory and attached a new cutting accessory to the shaft.

A proposed solution to reduce the undesirable heating of the nose of surgical tool system as well as the accessory disposed in the nose is to flow fluid through or around the nose. This fluid is typically sterile water or saline. A known surgical tool system of this design has a nose into which plural longitudinally extending grooves are formed. A sleeve is disposed over the nose. During a procedure in which this assembly is used, the cooling fluid is flowed through these grooves. The sleeve prevents the fluid from flowing away from the nose until the fluid reaches the distal end of the nose. The fluid functions as a heat sink that extracts the heat from the nose and cutting accessory. The fluid flows the heat away from the tool system. This arrangement reduces the temperatures of the nose and cutting accessory from rising to the level at which when these components contact tissue, the tissue is subjected to potentially damage causing heating.

A disadvantage of the above assembly is that for the assembly to transfer a sufficient quantity of heat away from the nose and cutting accessory, a relatively large volume of irrigating fluid needs to be flowed through the nose. This fluid is discharged from the nose adjacent the site at which the cutting accessory needs to be applied. The presence of this fluid can interfere with the performance of the cutting accessory and obstruct the practitioner's view of the site at which the procedure is being performed. To prevent these undesirable consequences it may be necessary to almost continually apply suction to the site at which the procedure is being performed in order to draw this fluid away from the site. Having to perform this added step contributes to the complexity and/or time required to perform the procedure.

Another solution suggested to compensate for the friction induced heating of the nose of surgical tool system is place a wick of fluid retaining material over the wick. Prior to the use of the tool, a fluid, typically saline or sterile water, is coated over the wick. This fluid serves as a heat sink that absorbs the heat generated by the use of the tool. A disadvantage of this practice is that the fluid can absorb only so much heat before the fluid evaporates and is dispersed into the ambient environment as a gas, typically water vapor. Once the fluid has so evaporated, the wick has little thermal capacity to absorb the friction induced heat. If the surgeon wants to hold continue to maintain the nose below at a temperature below a below a certain level, the procedure needs to be interrupted in order to recoat the wick in a heat absorbing liquid.

SUMMARY OF THE INVENTION

This invention is directed to a new and useful surgical tool system. The surgical tool system of this invention is designed to extract the heat generated at the nose of a surgical handpiece so as to prevent the excessive heating of the nose and the cutting accessory disposed in the handpiece. The surgical tool system of this invention extracts this heat away from the handpiece without requiring the discharge of relatively large quantities of fluid at the site to which the system is applied.

It is a further object of this invention to provide an efficient means of producing a surgical handpiece with a nose of this invention.

The surgical tool system of this invention includes a surgical handpiece with an elongated nose. The handpiece of this invention is designed to actuate a cutting accessory. The cutting accessory has an elongated shaft. The shaft extends through a bore formed in the nose. In many versions of the invention the accessory shaft is rotated or reciprocated.

The handpiece nose is formed with an enclosed groove. The groove extends in a helical pattern such that, as the groove extends proximal to distally, the groove curves circumferentially around the nose. The groove thus curves circumferentially around the bore formed in the nose. A proximal end of the handpiece has a fitting into which irrigating solution is introduced into the groove. Adjacent the distal end of the nose, the groove is open. In some versions, the groove curves back to an outlet fitting.

In some versions of the invention, the nose includes a body and a shell disposed over the body. A groove is formed in the body. The shell is disposed over the body and the groove. The shell covers the groove so as to further define the enclosed channel.

In some versions of the invention, the outer shell is formed from a flexible material that is secured over the inner shell.

BRIEF DESCRIPTION OF THE DRAWINGS

The invention is pointed out with particularity in the claims. The above and further features and benefits of this invention are understood from the following Detailed Description taken in conjunction with the following drawings in which:

FIGS. 5, 6 and 7 are enlarged cross sectional views of sections of the front end attachment and cutting accessory;

FIG. 8 is a perspective view of the where the nose emerges from the head piece of the front end attachment;

FIG. 9 is a perspective view of distal end of the nose and the cutting accessory that emerges from the nose;

FIG. 10 is view of the nose and accessory of FIG. 1, the extent to which the outer sleeve is disposed over the distal end of the nose is seen;

FIGS. 15A, 15B and 15 *c* are, respectively, top, side and bottom plan views of the nose of FIG. 14.

DETAILED DESCRIPTION

Figure 1:
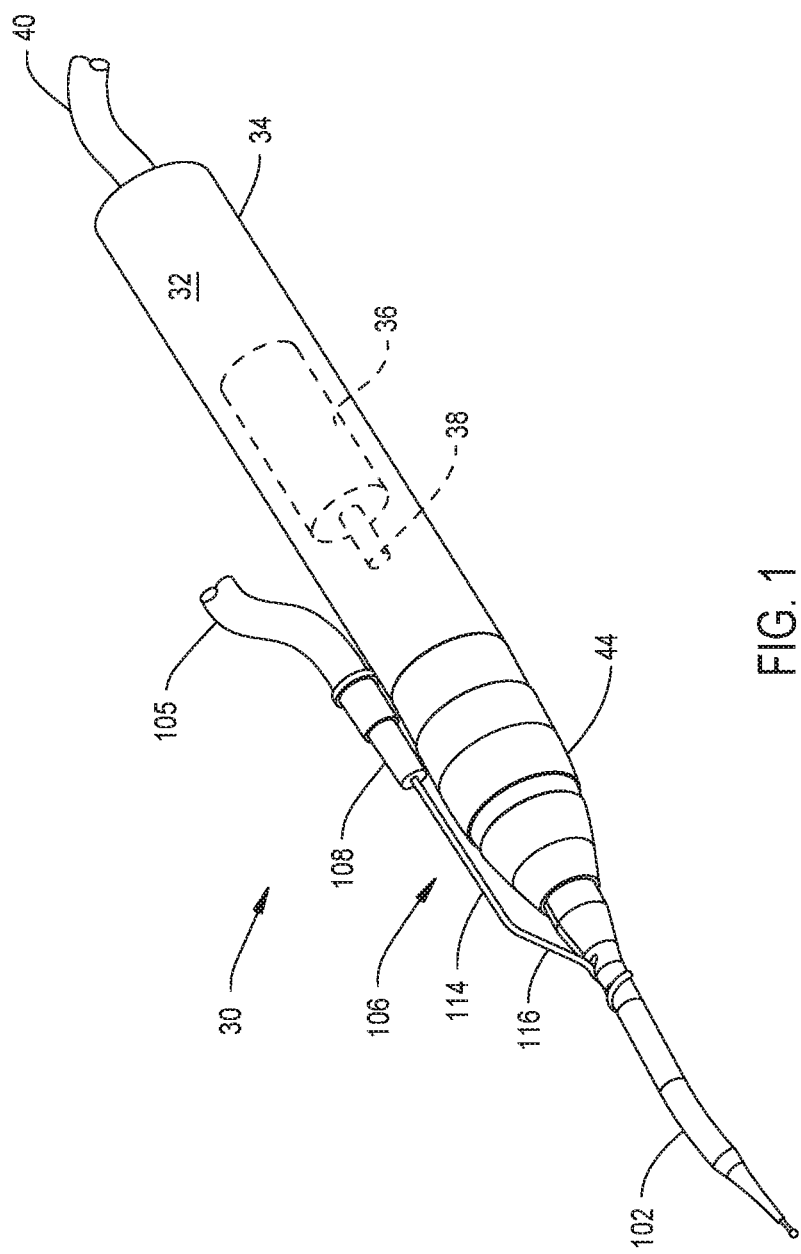
FIG. 1 is a perspective view of a surgical tool constructed in accordance with this invention.
Figure 2:
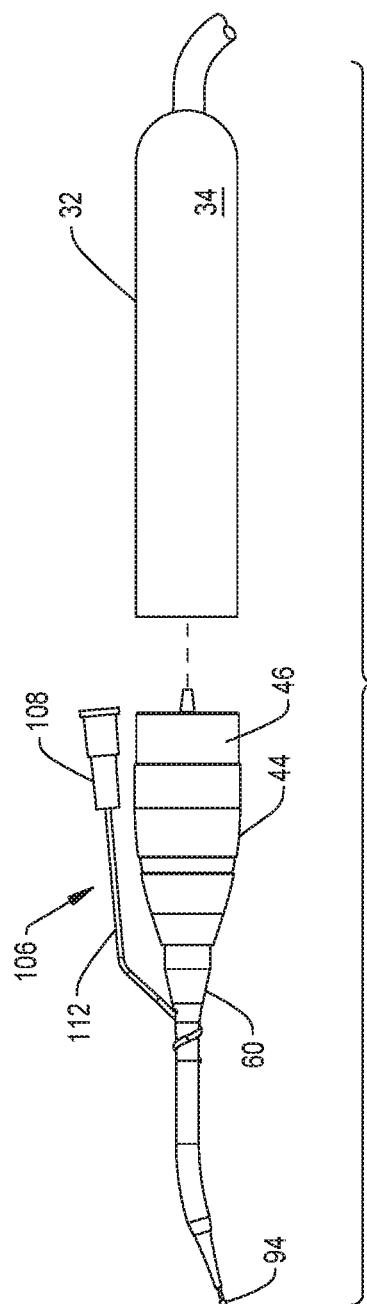
FIG. 2 is an exploded view depicting how the front end attachment and the cutting accessory are separate from the handpiece.

The basic components of a powered surgical tool 30, sometimes herein called a tool 30 or a tool system 30 or a system 30, are seen in FIGS. 1 and 2. Tool 30 includes a handpiece 32. Handpiece 32 has a body 34, alternatively referenced to herein as a housing 34. Disposed inside the handpiece body 34 is a motor 36, represented by a phantom cylinder. Motor 36 may be any motor used to drive a motor shaft 38, alternatively referenced herein as a handpiece shaft 38 or a handpiece drive spindle 38, represented by a smaller phantom cylinder. Motor 36 is typically an electrical, pneumatically or hydraulically driven motor. A cable 40 is shown extending proximally from the handpiece body 34. ("Proximal" is understood to mean towards the practitioner holding the handpiece, away from the site to which the handpiece is applied. "Distal" is understood to mean away from the practitioner, towards the site to which the handpiece is applied.) Cable 40 is the conduit over which electrical power, gas or a liquid is supplied to the motor 36 to drive the motor. It is also within the scope of this invention that motor 36 be battery powered.

Figure 3:
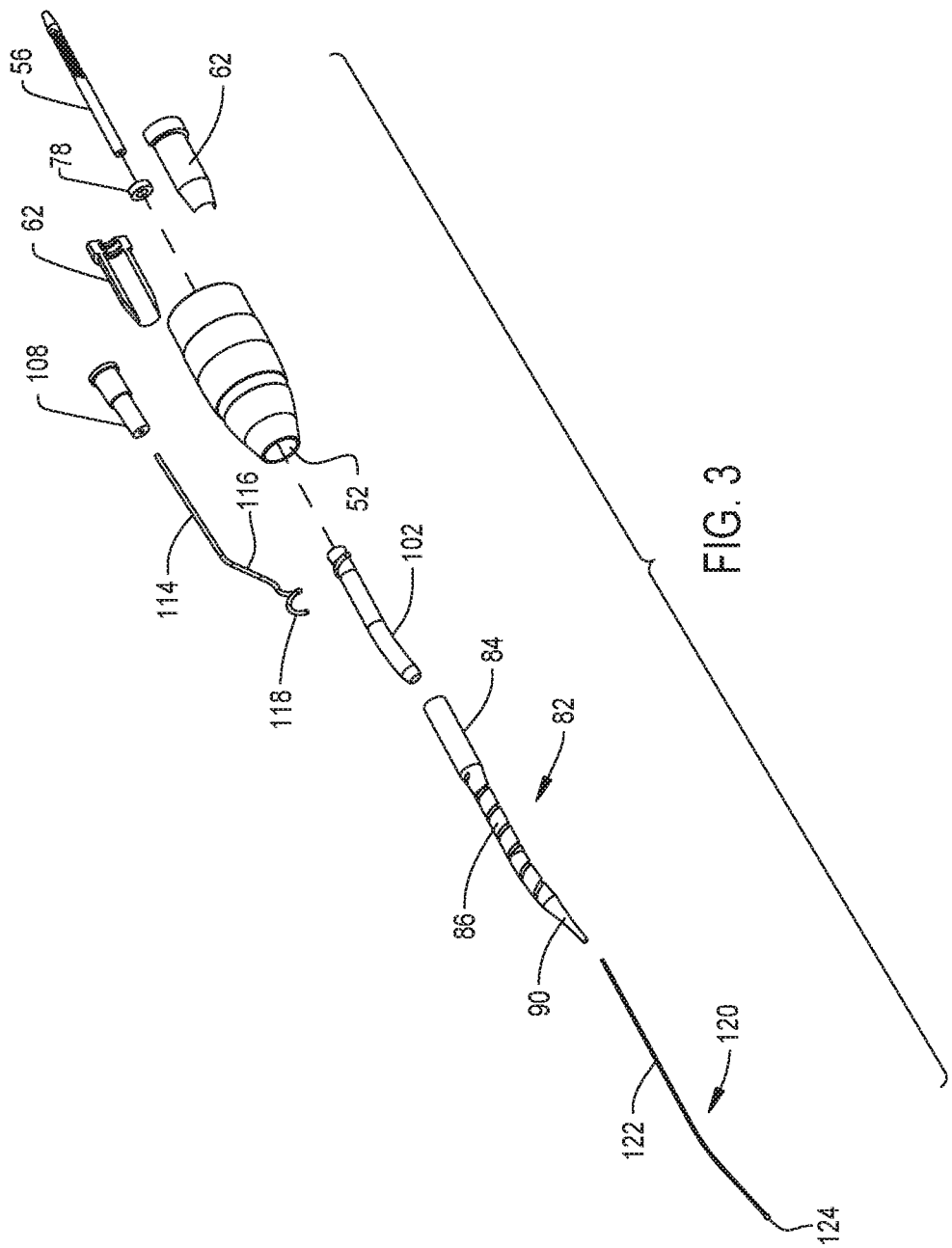
FIG. 3 is an exploded view of the front end attachment and cutting accessory.

A front end attachment 44 is removably attached to and extends distally forward from the handpiece body 34. An attachment drive shaft 56 is rotatably disposed in the front end attachment 44. When system 30 of this invention is assembled, shaft 56 engages the motor shaft 38 to be rotated by the motor shaft. A cutting accessory 120 is rotatably disposed in the front end attachment 44. Cutting accessory 120, as seen in FIG. 3, has an elongated shaft 122. Attachment drive shaft 56 and cutting accessory shaft 122 are formed with complementary features that facilitate the removable attachment of the two shafts. The accessory shaft 122 extends through and forward of the distal end of the front end attachment 44. In many versions of the invention the shaft 122 is formed so that the section of the shaft that extends through an attachment nose bore 92 has a constant diameter. Shaft 122 is understood to be flexible. This flexibility of the shaft 122 allows the shaft to bend as the shaft rotates in the bent section of nose bore 92.

A tissue working member 124 is attached to the distal end of the accessory shaft 122 so as to be located forward of the attachment 44. Tissue working member 124 is the component of the tool 30 that, when applied to tissue performs the desired surgical procedure. Tissue working member 124 is often a bur head or a drill bit.

Figure 4:
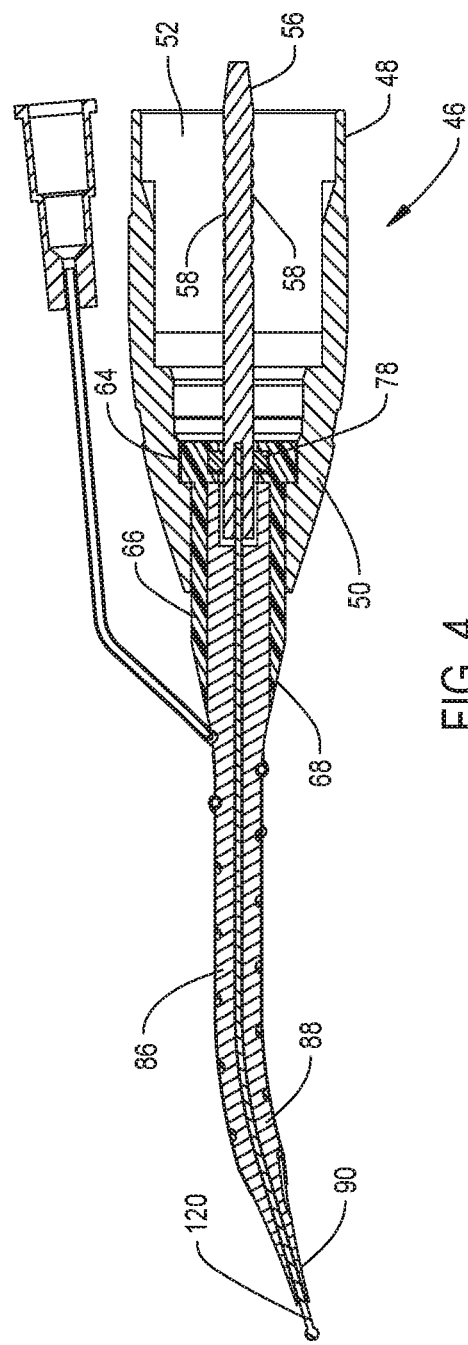
FIG. 4 is a cross sectional view of the front end attachment and cutting accessory.

From FIGS. 3 and 4 it can be seen that the front end attachment 44 includes an attachment cap 46 that forms the main housing of the attachment. Cap 46 has a proximal section 48 that is generally of constant diameter. Integral with and extending forward from the proximal section 48 cap 44 has a distal section 50. Extending distally from the proximal section 48, the diameter of the distal section 50 decreases. Internal to the cap 46 is a cap bore 52. Cap 46 is formed so that bore 52 has sections with different diameters. Generally, extending proximally to distally the diameter of the different sections of bore 52 decrease.

Not illustrated and not part of the present invention are features that facilitate the removable coupling of the front end attachment 44 to the handpiece body 34. One such set of features include providing the handpiece body 34 and attachment cap 46 with complementary threaded surfaces. In still other versions of the invention, one of the body 34 or cap 46 is provided with a snap ring or spring loaded leg; the other one of the cap 46 or body 34 is formed with a void space to receive this spring element. Also not shown and not illustrated are geometric features integral with the handpiece shaft and attachment shaft that facilitate the releasable coupling of these components. The incorporated by reference U.S. Pat. No. 5,888,200 discloses one such assembly. A variation on this tool system is disclosed in U.S. Pat. No. 6,562,055, (PCT Pub. No. WO 01/060261) entitled CUTTING ATTACHMENT FOR A SURGICAL HANDPIECE DESIGNED TO BE SELECTIVELY COUPLED TO THE HANDPIECE also incorporated herein by reference, discloses another assembly for holding an attachment shaft to the handpiece shaft. These incorporated by reference documents also disclose how a front end attachment can be held to a handpiece 32.

The attachment drive shaft 56 is rotatably disposed inside cap 46. In the illustrated version of the invention, the distal end of the drive shaft 56 extends proximally rearwardly out of the cap 46. The drive shaft 56 is shown to have indentations 58 on the outer surface of the shaft. The indentations receive locking features integral with the handpiece drive spindle 38. The seating of the handpiece locking features into the drive shaft indentations 58 hold the drive shaft to the handpiece drive spindle 38 so these two components rotate in unison. The exact means by which the attachment drive shaft 56 is held to the handpiece drive spindle is not part of the present invention. The incorporated by reference documents including the now incorporated by reference U.S. Pat. No. 8,597,316 PCT Pub. No. WO 2010/028001 disclose means by which these two components are releasably held together.

A sleeve 60 and a bearing assembly 78 cooperate to rotatably hold the attachment drive shaft 56 in cap 46. Sleeve 60 is formed from two sections 62 that a pressed together. The sleeve 60 is shaped to have a foot 64. Foot 64 forms the proximal end of the sleeve. Foot 64 is circular in shape and is the widest diameter portion of the sleeve 60. A sleeve stem 66 extends forward from foot 64. Sleeve stem 66 is cylindrical in shape and has a diameter less than that of the foot 64. The sleeve stem 66 is shaped to tightly fit in the most distal section of the cap bore 52. The components forming the attachment 44 are further formed so that sleeve stem 66 extends forward of cap 46. Forward of stem 66, sleeve 60 has a distal end tip 68. Extending distally forward from the stem 66, the outer diameter of the tip decreases.

A sleeve bore 70 identified in FIG. 5, extends proximally from the distal end the sleeve 60. Within the foot 64 there is a cylindrical sleeve void 72. An annular step 71 extends inwardly from and circumferentially around the inner wall of the sleeve 60 that defines the proximal end of bore 70. Step 71 separates bore 70 from void 72. Not identified but seen in FIGS. 4 and 5 are the opening in the proximal end of the sleeve 60 that opens into void 72. Also not identified is the opening defined by step 71 that is the opening between bore 70 and void 72.

Bearing assembly 78 rotatably holds the attachment drive shaft 56 to sleeve 60. The bearing assembly 78 is disposed in sleeve void 72. Drive shaft 56 extends through the bearing assembly 78. The drive shaft 56 extends into the proximal end of sleeve bore 70.

An attachment nose 82, also part of the front end attachment 44, is seated in and extends forward from cap 46. Nose 82 is a single piece component formed from stainless steel, plastic, aluminum or a ceramic. The nose 82 has three main sections 84, 86 and 90 each of which is general circular in cross sectional shape. A first section is the proximal section 84. Nose proximal section 84 is the widest diameter portion of the nose 82. The nose proximal section 84 is the portion of the nose 82 that is seated in sleeve bore 70. The nose proximal section 84 also extends a short distance forward of sleeve 60. A nose middle section 86 is located forward of proximal section 84. The middle section 86 has a diameter less than that of the proximal section 84. Not identified is the tapered transition section between nose sections 84 and 86. Nose middle section 86 is the longest of the three main nose sections. The illustrated attachment 44 is formed so that, proximal to the distal end of the middle section 86, the middle section is formed with bend 88. Distal to bend 88, is the nozzle distal section 90. Nose 82 is formed so that diameter of the distal section 90 decreases as the distal section extends forward from the middle section 86.

When the attachment 44 is assembled, the nose middle and distal sections 86 and 90, respectively, extend forward of sleeve 60. The maximum diameter of these sections of the nose 82 including the below discussed shell disposed over the nose is 10 mm and, in many versions of the invention, 5 mm or less.

Attachment nose 82 is further formed so that a bore 92, identified in FIGS. 6 and 7, extends proximally through the nose from the distal end of distal section 90. Bore 92 is centered on the distal-to-proximal longitudinal axis through the nose 82. In versions of the invention in which nose 82 is formed with bend 88, bore 92 has a bend. Bore 92 is dimensioned to receive cutting accessory 120 so the accessory shaft 122 can rotate in the bore. At the proximal end of the nose 82, within proximal section 84, bore 92 opens into a counterbore 94, seen in FIG. 5. Counterbore 94 is wider in diameter than bore 92. Counterbore 94 is dimensioned to receive the attachment drive shaft 56 so the drive shaft 56 can rotate in the nose 82.

Nose 82 is also formed to have a nose groove 96 that extends proximally to distally along the outer surface of the nose. More specifically, the groove 96 extends in a helical pattern around the nose. The proximal end of the groove 96 is adjacent the proximal end of nose middle section 86. When the groove reaches the nose distal section 90, the groove extends linearly. Groove 96 terminates approximately 5 to 10 mm proximal from the distal end of the nose 82.

A shell 102 is disposed over nose 82. In some versions of the invention, shell 102 is a section of heat shrink tubing. The shell 102 is disposed over nose 82 to extend over groove 96. In many versions of the invention the shell does not extend over the whole of groove 96. More specifically, the shell does not extend over the portion of the nose in which the distal end of groove 96 is formed. In the illustrated version of the invention, the proximal end of the shell is located distally forward of the portion of nose middle section 86 in which the proximal most turns of groove 96 are formed. Shell 102 also does not extend over the portion of groove 96 formed in the nose distal section 90. Thus, as seen in FIG. 10, the distal end of groove 96 is open to the environment.

Attachment 44 also includes an irrigation fitting 106. Fitting 106 includes a head 108. Head 108 is generally in the form of a tube that is open at the proximal end. Head 108 is dimensioned to receive a tube 105 (FIG. 1) in the open proximal end. A tube 112 extends from the distal end of fitting head 108. The tube 112 is in fluid communication with the bore that extends through the head (bore head not identified). Tube 112 has a main section 114 that extends from head 108. Tube main section 114 is generally coaxial with head 108. At the distal end of the main section a leg 116 angles away from the main section. A foot 118 which extends forward from leg 116 is the most distal portion of the tube 112. Foot 118 is helical in shape. More particularly foot 118 is designed to seat in the in groove 96 formed in nose 82.

In some versions of the invention, fitting foot 118 is secured in nose groove 96 by a friction compressive fit. Once the fitting is so secured, shell 102 is secured over nose 82. In some versions of the invention the securing of the shell 102 over the nose 82 and fitting foot 118 secures the fitting 106 to the nose. The components of this invention are designed so that the open distal end of fitting tube 112 opens into a portion of the nose groove 96 that is covered by shell 102.

Cutting accessory 120 has shaft 122 able to rotate in attachment nose bore 92. In the described version of the invention, bore 92 is angled. Accordingly, in this version of the invention, shaft 122 is sufficiently flexible so as to be able to rotate in the bent portion of bore 92. The proximal end of the accessory shaft 122 is formed with features designed to facilitate the removably coupling of the shaft to the attachment drive shaft 56. In the illustrated version of the invention, the proximal end of the accessory shaft is dimensioned to simply press fit in a bore that extends proximally from the distal end of drive shaft 56. The specific features integrally with these two shafts 56 and 122 are beyond the scope of the present invention.

Surgical tool 30 of this invention is prepared for use by coupling front end attachment 44 to the handpiece 32. The cutting accessory 120 is coupled to the attachment. Cable 40 is connected to the device that provides power to motor 36. A tube 105 that is connected to a source of irrigating fluid is attached to fitting head 108. Once these connections are made, tool 30 is ready for use. Owing to the small diameter of the nose 82, front end attachment 44 of this invention can be used to direct the cutting accessory 120 through a portal or opening in the patient that is relatively small in size to the site internal to the patient at which the accessory is to be applied. In some versions of the invention, the distal section of the nose may have a maximum diameter of 3 mm. In these versions of the invention the bore 92 internal to the nose, including the bent section of the bore that extends through bend 88, may have a diameter of 1.5 mm or less and in some versions of the invention 1.0 mm or less. A bore 92 with a diameter of 1.5 mm is able to receive the shaft 122 of a cutting accessory that has a diameter of 1.0 mm or less. A bore 92 with a diameter of 1.0 mm is able to receive a cutting accessory with a shaft 122 having a diameter of 0.5 mm or less. The tissue working member of this type of cutting accessory may have a diameter of 0.7 mm or less. These versions of the invention may be inserted in portals, openings in the patient, that are no wider than the diameter need to facilitate the insertion of nose in the patient.

Tool 30 is used like a conventional tool. When there is a need to use the cutting accessory 120, motor 36 is actuated. The rotational moment output by the motor 36 is transferred from the handpiece shaft 38, the attachment shaft 56 and the accessory shaft 122 to the tissue working member 124. The tissue working member is applied against tissue to perform the desired surgical procedure.

The nose of this invention does not include any low friction bearings in the bore 92 between the inner surface of the bore and the accessory shaft 122 that minimize the generation of friction induced heating that occurs when the shaft rubs against the inner surface of the nose that defines bore 92. The rotation of the cutting accessory shaft 122 in nose 82 causes the friction of the movement of the shaft to generate heat in the nose and shaft. This heat is especially prone to occur in the bent section of the nose. This is because in this section of the nose, the bent section of the shaft continually rubs against the bent section of the inner surface of the nose that defines the bend in the bore 92. To prevent this heat from inducing an unacceptable temperature rise in nose 82 or cutting accessory 120, irrigating fluid is flowed from tube 105 and fitting 106 into the enclosed channel defined by nose groove 96 and the portion of shell 102 disposed over the nose 82. This fluid functions as a heat sink that draws away the friction-generated heat from the nose 82 and cutting accessory 120. Groove 96 has an unwound length that, at a minimum, is 1.05 times greater than the length of the narrow diameter portion of the nose and tube 112 that extends forward from the cap 46 or any sleeve integral with the cap. This is the portion of the nose understood to have a diameter of 10 mm or less and often 5 mm or less. In still more preferred versions of the invention, the unwound length of the groove is 1.25 times or greater than this length. This means that over the length of the small diameter portion of the nose 82, there is a relatively large surface area between the surface of the nose and the fluid that functions as a heat sink. Consequently, a significant amount of the thermal energy, the heat, generated by rotation of the cutting accessory 120 is drawn away from both the nose 82 and the cutting accessory. This reduces the extent to which the temperature of these components rise to the level at which they may transfer heat to the tissue that results in the thermally induced damage of the tissue.

A further feature of this version of the invention is that the quantity of irrigating fluid that is flowed through the nose and discharged adjacent the site to which the tissue working member is applied is held to a minimum. More specifically invention, where there is a single channel through the nose discharges less fluid than an assembly wherein there are plural channels each channel having the same cross sectional area as the channel in a nose with a single channel.

Likewise this invention allows the system 30 to include a cutting accessory 120 with a shaft 122 that, is not formed so that the section of the shaft seated in the bent section of the bore 92 has, in comparison to other sections of the shaft 122 a reduced diameter. This reduces the likelihood that, the continued bending of this section of the shaft 122 will stress the shaft to the point that shaft fractures and is rendered unusable.

Figure 11:
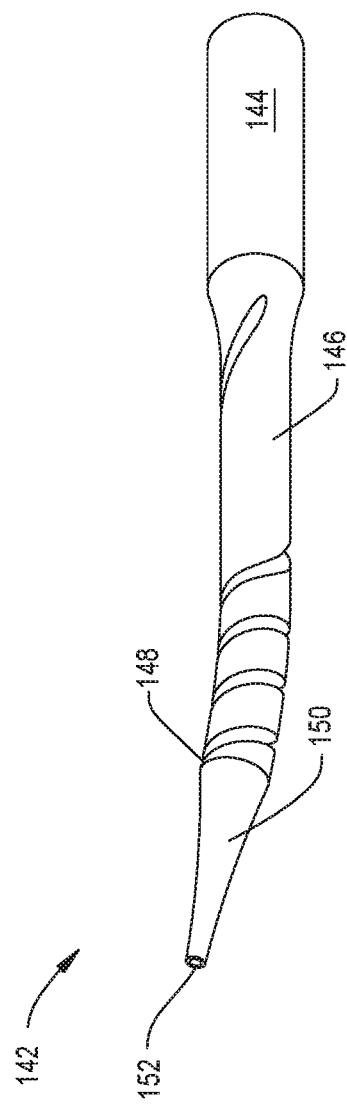
FIG. 11 is a perspective view of an alternative nose, with the shell removed, of this invention.
Figure 12:
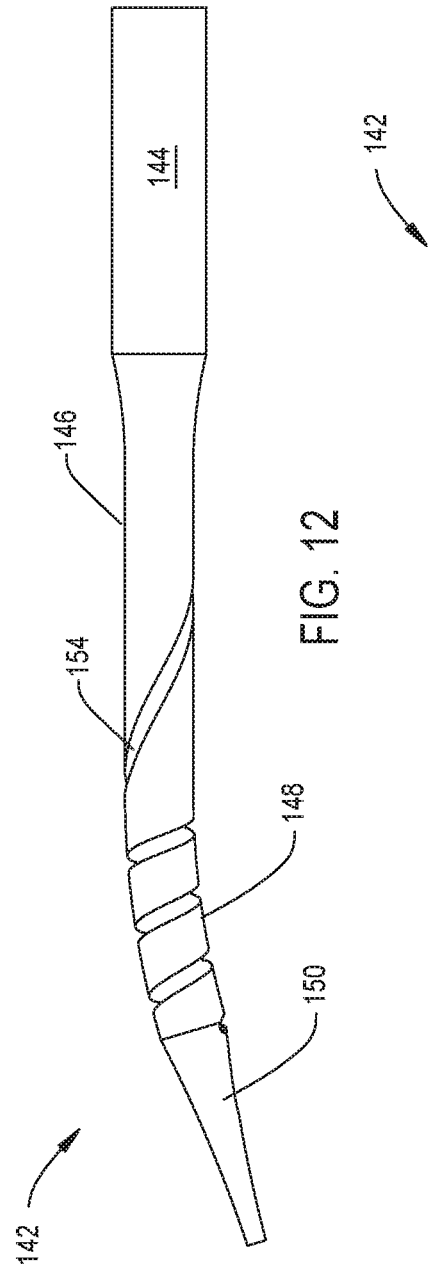
FIG. 12 is a side plan view of the nose of FIG. 11.
Figure 13:
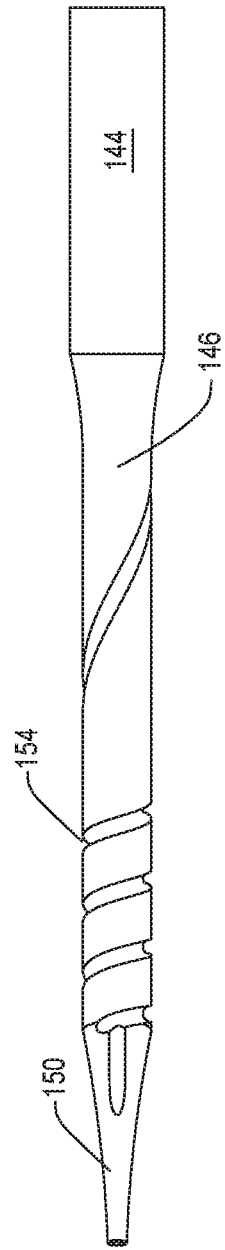
FIG. 13 is top plan view of the alternative nose of FIG. 11.
Figure 14:
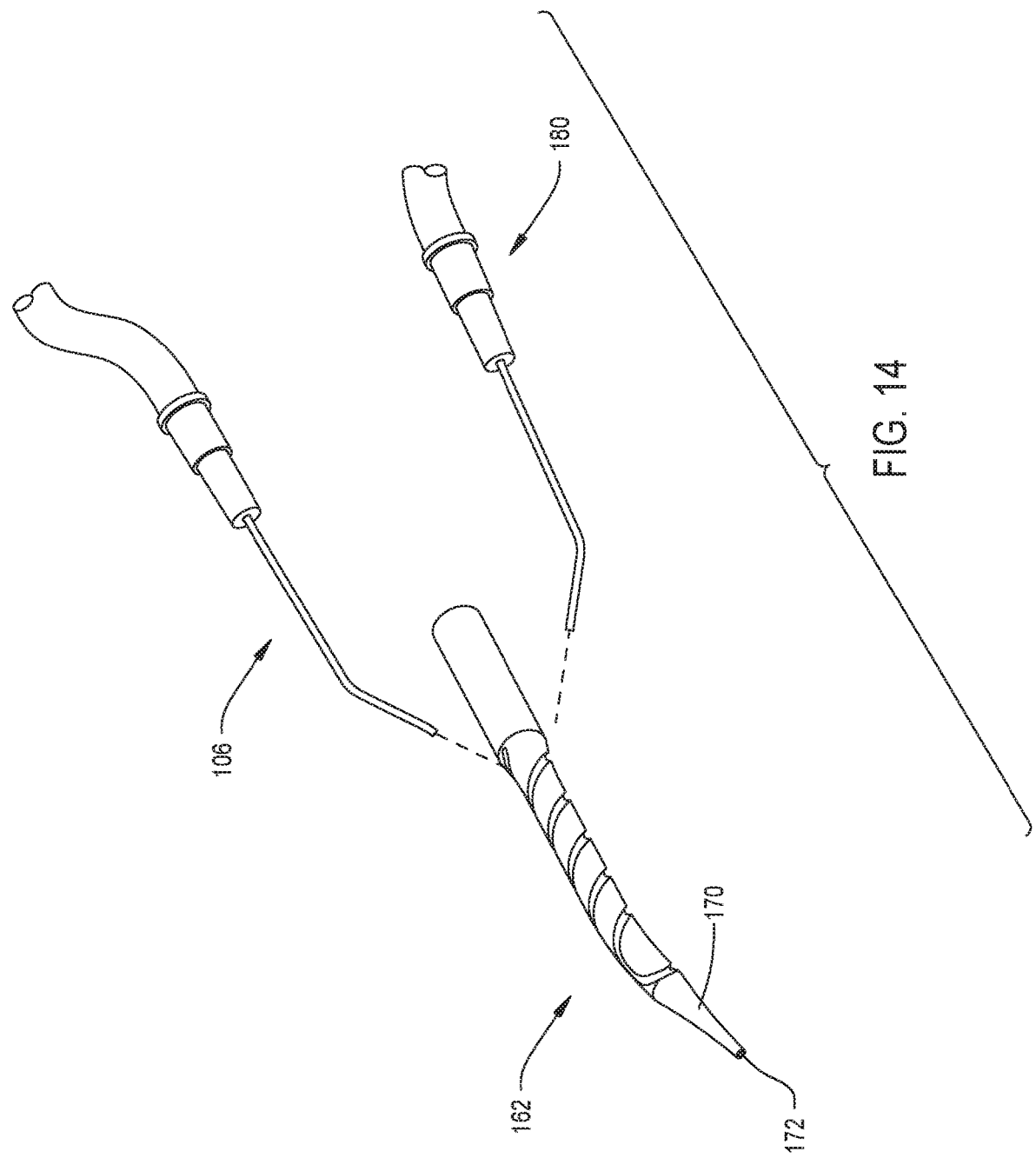
FIG. 14 is an exploded view of an alternative nose and the fittings that are attached to the nose of this invention.

FIGS. 11, 12 and 13 depict the structure of an alternative nose, nose 142, that may be incorporated into this invention. Nose 142 has a proximal section 144, a middle section 146 and a distal section 150 similar to the sections 84, 86 and 90, respectively of nose 82. Nose 142 is further formed to have a bend 148 analogous to bend 88 of nose 82. A bore 152, the open end of which, extends longitudinally axially through the nose 142. Bore 152 is analogous to bore 92 of nose 82.

A groove 154 is formed in nose 142. A difference between groove 154 and groove 96 of nose 82 is that groove 154 has a variable pitch. Here "pitch" is understood to be to be the length of groove along the nose for each 360° turn of the groove. More particularly groove 154 has a relatively large pitch where the nose is straight. Thus, groove 154 has a relatively large pitch along the proximal portion of the middle section 146 where, groove 154 has a relatively large pitch. Around bend 148, the pitch is relatively small. While not seen it is understood that nose 142 is covered with an outer shell similar to the shell 102. The portion of the shell disposed over the groove 154 covers the groove so as to form the enclosed fluid channel in the nose.

When a tool system with nose 142 is actuated, the greatest rubbing of the accessory shaft 122 against the nose occurs within the portion of the nose forming bend 148. This means that the bent section of nose 142 is the location where some of the greatest frictionally heating of the nose and accessory shaft occurs. In this version of the invention, owing to the relatively small pitch of groove 154 this is the section of the tube wherein, in terms of surface area, there is the largest interface between the nose and irrigating fluid. This results in relatively large drawing away of the heat generated in this section of the nose.

As discussed above, proximal to this location the groove has a relatively large pitch. A benefit of this design is related to fact that when the groove of this invention is present, the absence of nose forming material inherently reduces the mechanical strength of the nose. This is in comparison to a nose that does not have the groove. However, in this design at the location where large quantity of heat is not generated, since the groove is of large pitch, the amount of material absent from the nose to form the groove is less than what would be absent if the groove had a small pitch. This means that the section of nose 142 with the large pitch groove has greater mechanical strength than what would be present if this section of the groove is formed with a pitch identical or similar to the groove pitch where bend 148 is present. Thus, this version of the invention provides the heat sinking properties of the irrigation fluid without significantly sacrificing the structural strength of the nose where the benefits of the fluid are less needed.

Still a further feature of the above version of the invention is that can require less time to machine a nose have a groove with a large pitch section than a nose with that has small pitch groove.

FIGS. 14 and 15A through 15C illustrate an alternative version of the invention. Nose 162 has a proximal section 164, a middle section 166 and a distal section 170 similar to the sections 84, 86 and 90, respectively of nose 82. Nose 142 is further formed to have a bend 168 analogous to bend 88 of nose 82. A bore 172, the open end of which, extends longitudinally axially through the nose 162. Bore 172 is analogous to bore 92 of nose 82.

A groove 174 is formed in nose 142. The groove 174 is formed in the nose middle section 166. A difference between groove 154 and groove 96 of nose 82 is that groove 154 does not have an open end at the nose distal section 170. Instead, immediately distal to bend 168, the groove loops back around the nose 162. The groove 174 extends back along the nose proximal section 164. The groove 174 thus has two ends adjacent the nose proximal section 164.

The previously described fitting 106 is fitted to nose 162 to be open into one end, end 173 of groove 174. A second fitting, fitting 180, is fitted to the second end, end 175 of groove 174. Not seen is the shell analogues to shell 102 that is seated over the nose 162.

During use of this version of the invention, fluid is introduced into the groove through fitting 106 as in the prior described versions of the invention. The fluid that flows through groove 174 is not discharged. Instead the fluid flows through out through fitting 180 An advantage of this version of the invention is that it provides the cooling advantage of the fluid without requiring the discharge of fluid at the site to which the tool is applied.

The above is directed to specific versions of the invention. Other versions of the invention may have features different from what has been described.

For example, in some versions of this invention, the small diameter nose of this invention may be built directly into the handpiece 32. Thus, in these versions of the invention there is no removable front end attachment. In these versions of the invention, the cutting accessory shaft is directly coupled to a rotating output shaft that is actuated by the motor. In these versions of the invention the handpiece has a coupling assembly that releasably holds the accessory shaft to the handpiece output shaft.

Similarly, there is no requirement that in all versions of the invention, the nose be bent. Likewise, in some versions of the invention, the nose may have plural bends. In versions of the invention with wherein the nose has plural bends the enclosed channel through which the irrigation fluid flows may have plural spaced apart section wherein the channel has a relatively small helical pitch.

In some versions of the invention, fitting 106 is welded, braised or glued to the nose 82.

Likewise, the front end attachment is not limited to tools that include a motor driven cutting accessory. The front end attachment of the tool of this invention may be a device that is vibrated using transducers. Alternatively, the cutting accessory of this invention may be a device that applies thermal energy or photonic energy (light) to the site to which the accessory is applied. The front end attachment of this invention will be useful to prevent any heat that is being generated from radiating outwardly from a location other than at the distal end tip of the accessory.

Further, the nose of this invention may be structured out of components different from what has been described above. Thus there is no requirement that the enclosed channel through which the irrigating fluid flow always be defined by a nose formed with a groove and a shell heat shrinked over the tube. In one alternative version of the invention, the nose may consist of an inner shell over which a rigid outer shell is secured. The channel may be defined by a groove in the outer surface of the inner shell. Alternatively, or in combination with this first groove the channel may be defined by a groove formed in the surface of the inner shell disposed over the outer shell. In still other versions of the invention the nose may be a monolithic component in which the groove is formed. For example, the nose by formed by molding metal, plastic or ceramic. Internal to the mold used to define the nose there is a first mandrel and a second mandrel. The second mandrel is helically shaped and surrounds the first mandrel. The first mandrel defines the bore in which the accessory shaft is disposed. The second mandrel defines the enclosed channel. As a result of the molding process and the removal of the mandrels, the nose includes the bore for the accessory and the enclosed channel through which irrigation fluid is flowed.

Accordingly, it is an object of the appended claims to cover all such modifications and variations that come within the true spirit and scope of the invention.

What is claimed is:

1. A front end attachment for a powered surgical tool, the front end attachment comprising:
   a nose that extends forward from a proximal end of the nose, the nose defining:
   a bore for receiving a shaft of a cutting accessory connectable to a motor of the powered surgical tool for rotation thereby, and
   an enclosed channel separate from the bore, the channel extending longitudinally and helically along the nose such that, as the channel extends longitudinally, the channel curves around the nose so as to curve around the bore; and
   an irrigation fitting in fluid communication with the enclosed channel in the nose that is adapted to receive an irrigating fluid and flow the fluid through the enclosed channel.

2. The front end attachment of claim 1, wherein the nose is further constructed so at least the section of the nose around in which the enclosed channel is formed does not have any bearings in the bore.

3. The front end attachment of claim 1, wherein the front end attachment is removably attachable to a housing of the powered surgical tool.

4. The front end attachment of claim 1, wherein:
   a groove is formed in an outer surface of the nose; and
   a shell is disposed over the outer surface of the nose so as to extend over and enclose the groove so that portions of the nose that define the groove and the shell collectively define the enclosed channel.

5. The front end attachment of claim 1, wherein:
   the nose is further formed so as to have an outlet opening adjacent a distal end of the nose; and
   the enclosed channel is in fluid connection with the outlet opening in the nose.

6. The front end attachment of claim 1, wherein:
   the nose includes a distal section that defines a distal end of the nose that can receive the shaft of the cutting accessory, the distal section having an outer surface in which a groove is formed; and
   the enclosed channel directly opens up into a proximal end of the groove formed in the distal section of the nose.

7. The front end attachment of claim 1, wherein the nose is further formed so the enclosed channel has an outlet opening located adjacent a proximal end of the nose.

8. The front end attachment of claim 1, wherein the nose is formed so that the enclosed channel includes at least one turn, the turn extending circumferentially around the bore.

9. The front end attachment of claim 1, wherein the nose is formed so that the enclosed channel includes plural turns, at least two of the turns each circumferentially around the bore.

10. The front end attachment of claim 1, wherein:
    the nose is formed to define a bent section of the nose with the bore within the bent section being bent; and
    the nose is further formed so that a helix defined by the helically extending enclosed channel varies along a length of the nose such that along a portion where the nose is straight, the enclosed channel has a first pitch and, where the nose is bent, the enclosed channel has a second pitch smaller than the first pitch.

11. A front end attachment for a powered surgical tool, the front end attachment comprising:
    a nose that extends forward from a proximal end of the nose, the nose being formed with:
    a first section and a second section with the second section being located distal to the first section and forming a distal end of the nose and the second section being shaped to have a taper such that the second section has a diameter that decreases as the second section extends from the first section,
    a bore extending through the first and second sections with the bore dimensioned to receive a shaft of a cutting accessory that is connectable to a motor of the powered surgical tool for rotation in the bore by the motor,
    an enclosed channel that extends around the first section of the nose with the enclosed channel extending helically along the nose such that, as the channel extends longitudinally along the first section of the nose, the enclosed channel curves around the first section of the nose so as to curve around the bore, and an exposed groove formed in an outer surface of the second section of the nose, wherein the enclosed channel is in fluid communication with a distal end of the exposed groove; and an irrigation fitting in fluid communication with the enclosed channel in the nose that is adapted to receive an irrigating fluid so the irrigating fluid may flow through the enclosed channel and be discharged from the groove.

12. The front end attachment of claim 11, wherein the nose is further formed so the enclosed channel of the first section of the nose has a distal end that opens directly into a proximal end of the groove of the second section of the nose.

13. The front end attachment of claim 11, wherein the nose is further constructed so any section of the nose around in which the enclosed channel is formed does not have any bearings in the bore.

14. The front end attachment of claim 11, wherein:
the exposed groove formed in the second section of the nose is a first groove of the nose;
a second groove of the nose is formed in an outer surface of the first section of the nose; and
a shell is disposed over the outer surface of the second section of the nose so as to extend over and enclose the second groove so that portions of the nose that define the second groove and the shell collectively define the enclosed channel.

15. The front end attachment of claim 11, wherein the front end attachment is removably attachable to a housing of the powered surgical tool.

16. The front end attachment of claim 11, wherein the nose is formed so that the enclosed channel includes at least one turn, the turn extending circumferentially around the bore.

17. The front end attachment of claim 11, wherein the nose is formed so that the enclosed channel includes plural turns, at least two of the turned each circumferentially around the bore.

18. The front end attachment of claim 11, wherein:
the nose is formed to define a bent section of the nose with the bore within the bent section being bent; and
the nose is further formed so that a helix defined by the helically extending enclosed channel varies along a length of the nose such that along a portion where the nose is straight, the enclosed channel has a first pitch and, where the nose is bent, the enclosed channel has a small pitch that is smaller than the first pitch.

19. The front end attachment of claim 11, wherein the enclosed channel is at least partially enclosed by a shell that extends along the first section of the nose.

20. The front end attachment of claim 11, wherein the second section of the nose is formed a single exposed groove that is fluid communication with the enclosed channel.

* * * * *